(12) United States Patent
Haack et al.

(10) Patent No.: US 7,297,687 B2
(45) Date of Patent: Nov. 20, 2007

(54) METHOD OF TREATING INFECTIOUS DISEASES WITH POLYSACCHARIDE DERIVATIVES

(75) Inventors: Vera Haack, Jena (DE); Thomas Heinze, Jena (DE); Michaela Schmidtke, Jena (DE); Ute Möllmann, Jena (DE); Hans-Martin Dahse, Weimar (DE); Albert Härtl, Jena (DE)

(73) Assignee: Wolff Cellulosics GmbH Co. KG (DE)

( * ) Notice: Subject to any disclaimer, the term of this patent is extended or adjusted under 35 U.S.C. 154(b) by 213 days.

(21) Appl. No.: 10/500,807

(22) PCT Filed: Jan. 10, 2003

(86) PCT No.: PCT/DE03/00095

§ 371 (c)(1),
(2), (4) Date: Oct. 18, 2004

(87) PCT Pub. No.: WO03/057227

PCT Pub. Date: Jul. 17, 2003

(65) Prior Publication Data

US 2005/0054609 A1 Mar. 10, 2005

(30) Foreign Application Priority Data

Jan. 10, 2002 (DE) ................. 102 00 717

(51) Int. Cl.
*A61K 31/718* (2006.01)
*A61K 31/715* (2006.01)
*C08B 31/00* (2006.01)

(52) U.S. Cl. .................... 514/60; 514/54; 536/102; 536/45

(58) Field of Classification Search ............ 514/60, 514/54; 536/102, 45
See application file for complete search history.

(56) References Cited

U.S. PATENT DOCUMENTS

| 4,708,951 A | 11/1987 | Inagaki et al. ........... 514/57 |
| 5,049,383 A | 9/1991 | Huth et al. .............. 424/405 |
| 5,595,980 A | 1/1997 | Brode et al. ............. 514/57 |
| 5,731,259 A | 3/1998 | Palumbo et al. .......... 502/404 |
| 6,306,835 B1 | 10/2001 | Daly et al. .............. 514/55 |

FOREIGN PATENT DOCUMENTS

| EP | 0 948 960 | 10/1999 |
| JP | 05-295002 | 11/1993 |
| WO | 98/29099 | 7/1998 |
| WO | 00/26447 | 5/2000 |

OTHER PUBLICATIONS

Database WPI Section Ch, Week 199216 Derwent Publications Ltd., London, GB; AN 1992-126185 XP002242820 & JP 04 057969 A (Unitika Ltd), Feb. 25, 1992.

Science, vol. 257, Aug. 21, 1992, pp. 1055-1063, Barry R. Bloom, Christopher J.L. Murray, "Tuberculosis: Commentary on a Reemergent Killer".

Bundesgesundheitsblatt [Federal Health Newspaper] 38, (month unavailable) 1996, pp. 170-178, M. Kresken, "Prävalenz der Resistenz bei klinisch wichtigen Bakterienspezies gegenüber älteren und neueren Antibiotika in Europa".

Antiviral Research, 19, (month unavailable) 2001, pp. 55-69, Peter Wutzler, Rudolf Thust, "Genetic risks of antiviral nucleoside analogues a survey".

Antimicrobial Agents and Chemotherapy, 39, Jul. 1995, pp. 1632-1635, G. Andrei, R. Snoeck, and E. De Clerco, "Susceptibilities of Several Drug-Resistant Herpes Simplex Virus Type 1 Strains to Alternative Antiviral Compounds".

Antimicrobial Agents and Chemotherapy, 39, Dec. 1997, pp. 2686-2692, I. Pavic et al, "Flow Cytometric Analysis of Herpes Simplex Virus Type 1 Susceptibiltiy to Acyclovir, Ganciclovir, and Foscarnet".

(Continued)

*Primary Examiner*—Shaojia Anna Jiang
*Assistant Examiner*—Michael C. Henry
(74) *Attorney, Agent, or Firm*—Connolly Bove Lodge & Hutz LLP

(57) ABSTRACT

The present invention relates to a method of treating infectious diseases, that involves: (a) providing an alpha-glycosidically linked starch polysaccharide derivative; and (b) inhibiting the growth of an infectious disease by administering a composition comprising the alpha-glycosidically linked starch polysaccharide derivative. The alpha-glycosidically linked starch polysaccharide derivative represented by the following general formula I,

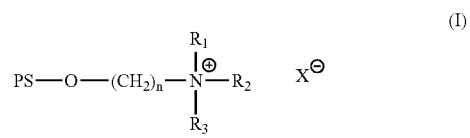

in which: the alpha-glycosidically linked starch polysaccharide derivative has a degree of quaternary ammonium group substitution of from 0.4 to 2.0; n is 2-4; $R_1$ is selected from the group consisting of $C_{1-4}$ alkyl, benzyl and benzyl substituted with a member selected from the group consisting of $C_{1-3}$ alkyl, halogen, alcoxy, carbamoyl, alkoxycarbonyl, cyano, dialkylamino and hydrogen; $R_2$ and $R_3$ are each independently selected from the group consisting of $C_{1-4}$ alkyl, benzyl and benzyl substituted with a member selected from the group consisting of $C_{1-3}$ alkyl, halogen, alcoxy, carbamoyl, alkoxycarbonyl, cyano and dialkylamino; and X is an anion selected from the group consisting of halide, hydroxide, sulfate, hydrogen sulfate and carboxylate.

14 Claims, No Drawings

OTHER PUBLICATIONS

Journal of Controlled Release, 50, (month unavailable) 1998, pp. 145-152, El-Refaie Kenawy et al, "Biologically active polymers: synthesis and antimicrobial activity of modified glycidyl metharcrylate polymers having a quaternary ammonium and phosphonium groups".

Trends in Polymer Science, 4, No. 11, Nov. 1996, pp. 364-370, S.,D. Worley and G. Sun, Biocidal Polymers.

Macromol. Mater. Eng., 286, (month unavailable) 2001, pp. 63-87, Tatsuo Tashiro, Antibacterial and Bacterium Adsorbing Macromolecules.

J.M.S.-Rev. Macromol. Chem. Phys., C40(4), (month unavailable) 2000, pp. 273-308, Kailash C. Gupta and Majeti N.V. Ravi Kumar, "An Overview on Chitin and Chitosan Applications with an Emphasis on Controlled Drug Release Formulations".

Science and Technology of Polymers and Advanced Material, (month unavailable) 1998, pp. 493-512, William H. Daly et al, "Preparation and Potential for Application of Cationic Polysaccharides in Cosmetic Formulations".

Polym. Mat. Sci. Eng., 79, (month unavailable) 1998, pp. 220-221, William H. Daly et al, "Antimicrobial Properties of Quaternary Ammonium Cellulose and Chitosan Derivatives".

METHOD OF TREATING INFECTIOUS DISEASES WITH POLYSACCHARIDE DERIVATIVES

FIELD OF THE INVENTION

The invention relates to the use of substances based on oligosaccharides and poly-saccharides as antiinfective agents, such as antibacterial agents and antiviral agents. These antiinfective agents can be employed, for example, as preservatives in cosmetic and pharmaceutical formulations, as biologically active compounds in drug preparations, for the biocidal finishing of surfaces, of textiles and of packaging materials for, for example, foodstuffs or products which are used in medicine, biology and pharmacy, and for wound protection for use in the cosmetic and pharmaceutical industries, in agriculture and in the foodstuffs and feedstuffs industries.

BACKGROUND OF THE INVENTION

It is known that infections with bacterial pathogens are increasing globally and that antibacterial resistance is a general health problem in this connection. A worldwide increase in tuberculosis infections due to mycobacterial strains which, over the course of time, has become resistant to the usual therapeutic agents (B. R. Bloom, J. L. Murray, Science 257, 1992, 1055), and the treatment of infections due to multi-resistant staphylococci (M. Kresken, Bundesgesundheitsblatt [Federal Health Newspaper] 38, 1996, 170), make it necessary to design new active substances. Alternative active compounds, possessing new mechanisms of action, in particular for counteracting antibiotic resistance and for controlling bacterial infections when there is intolerance towards existing active compounds, are urgently required. While a significant advance in controlling life-threatening infections was achieved with the development of highly selective nucleoside and nucleotide virustatic agents, such as acyclovir, penciclovir, ganciclovir, sorivudine and cidofovir for herpes viruses, these therapeutic agents all have the same principle of action. They inhibit the viral DNA polymerase. Another disadvantage of these compounds is that they also interfere with the DNA metabolism of the infected cell and therefore harbor the risk of inducing mutagenic, teratogenic and oncogenic effects (Wutzler, P. Thust, R. Antiv. Res. 49, 2001, 55). Furthermore, when nucleoside and nucleotide virustatic agents have been used over long periods, resistance to these medicaments has been shown to develop both in infected cell cultures and in immunosuppressed patients (Andrei, G. et al. Antimicrob. Agents Chemother., 1995, 39, 1632; Pavic, I. et al. Antimicrob. Agents Chemother., 1997, 39, 2686). For this reason, it is necessary to additionally develop novel highly active antiviral prophylactic and therapeutic agents which have another mechanism of action.

The large group of biologically active substances includes quaternary ammonium compounds. They are able to destroy microorganisms such as bacteria and fungi. Low molecular weight quaternary ammonium salts are used as disinfectants or biocidal coating materials (J. Controlled Release 50, 1998, 145). A typical problem associated with the low molecular weight compounds is inadequate bioavailability which is caused, for example, by a variety of transport and breakdown processes. Polymeric quaternary amine-functionalized materials can be synthesized from commercial quaternary exchange resins, by the graft polymerization of polyurethanes with polybutadiene hydroxytelecheles or from polysiloxanes possessing primary alcohol functions in the side chain. These biocidal polymers usually have high production costs and are frequently toxic since they contain residues of the toxic monomers (Trends in Polymer Science 4, 1996, 364). In addition to this, the polymers may accumulate in an undesirable and dangerous manner in the body since they are not biologically degradable. Furthermore, synthetic polymers which contain cationic functions are used as dispersions for preserving wood (U.S. Pat. No. 5,049,383). Disadvantages of the synthetic polymers which contain cationic functions are the high costs of preparing them, their toxicity (contamination with residual monomer) and their stability towards biological degradation.

Polysaccharide derivatives possessing quaternary ammonium functions are known and have thus far been used, in particular, as surface improvement additives for the paper and textile industries and as consistency regulators in cosmetics, in connection with which they only have a low degree of substitution (DS) of <0.2. To date, nothing is known about their biological effects. On the other hand, starch ethers which contain long alkyl chains ($C_8$-$C_{22}$) and are bonded to the starch by way of silyl ether groups are reported to have antiinfective effects, especially antibacterial effects (JP 05295002). The low chemical stability of the alkyl silyl ethers of polysaccharides leads to an uncontrolled release of functional groups simply as a result of the effect of atmospheric moisture and consequently to a reduction in, or to the loss of, the biological activity (D. Klemm et al., Comprehensive Cellulose Chemistry, Wiley-VCH, 1998). In addition to this, low molecular weight silyl compounds are toxic. In addition, publications refer to cellulose fibers and chitosan derivatives which possess antibacterial activity (W. H. Daly, M. M. Guerrini, Polym. Mat. Sci. Eng. 79, 1998, 220). As a natural cationic polysaccharide, chitosan is the one which is most frequently described and is used as a fungicidal agent in cosmetics (T. Tashiro, Macromol. Mater. Eng. 286, 2001, 63, K. C. Gupta, M. N. V. R. Kumar, J. M. S.-Rev. Macromol. Chem. Phys. C40, 2000, 273). Disadvantages of these polysaccharides are that they are frequently contaminated with other biogenic substances, that they are expensive as a result of the elaborate isolation and purification methods required and their inherent structure, with the ammonium groups being exclusively located on the polymer backbone. In addition to this, it is not possible to control their distribution and the content is limited to a degree of substitution of 1. Superabsorbers composed of cationically modified and crosslinked polysaccharides such as cellulose (EP 0 582 624 B1) have also been described.

While there are statements in the literature to the effect that the biological activity results from the presence of the quaternary ammonium functions, it is reported, on the other hand, that, as can be shown, typical compounds possessing cationic tetra-alkylnitrogen groups, such as polyquaternium 10, do not possess any bioactivity (W. A. Daly, M. M. Guerrini, D. Culberson, J. Macossay, in: Science and Technology of Polymers and Advanced Materials, Plenum Press 1998, 493). It is in no way possible to conclude from the results which are available in the literature whether the structures, and if so which, are in fact biologically active.

SUMMARY OF THE INVENTION

The invention is based on the object of finding polymers which have a novel anti-infective activity; the substances should have a powerful antiinfective effect over a broad spectrum, should make it possible to effectively combat antibiotic resistance in association with bacterial infections, should offer new possibilities for treating viral infections and should be well tolerated, biologically degradable, non-toxic and easy to prepare.

According to the invention, the object is achieved by providing polysaccharide derivatives in which etherification reactions have been used to introduce cationic functions with a degree of substitution (DS) in the range from 0.4 to 3.0, in particular alkylanimonium groups with a DS in the range from 0.6 to 1.8, into polysaccharides by way of spacer groups. Because of their biological degradability and non-toxicity, polysaccharides are particularly suitable.

The invention consequently relates to the use of polysaccharides, which are substituted, with a degree of substitution of from 0.4 to 3.0, by quaternary ammonium groups which are bonded by way of linkers, as antiinfective agents and/or for treating infectious diseases.

amylose, amylopectin and waxy corn starch, and also starches, such as the hylon types, which have been obtained from genetically modified plants, are used for preparing the active compounds according to the invention. The content of amylose in the starches, like that of amylopectin, can in each case be from 0 to 100%, preferably from 30 to 70%. The molecular weights of suitable polysaccharides are in the range of $10^3$-$10^7$ g/mol (cf. tab. 1). The anhydroglucose unit repeating units (AGU) can be linked to each other by way of α(1-4), α(1-6), α(1-3), β(1-4) and β(1-3) bonds or combinations thereof, such as α(1-4) and α(1-6), as shown diagrammatically in FIG. 1, or α(1-6), α(1-3) and α(1-4), and contain side chains which are differing lengths and which are linked in different ways. In addition to this, other functional groups, such as phosphate ester functions, can also be present, for example in the case of natural potato starch.

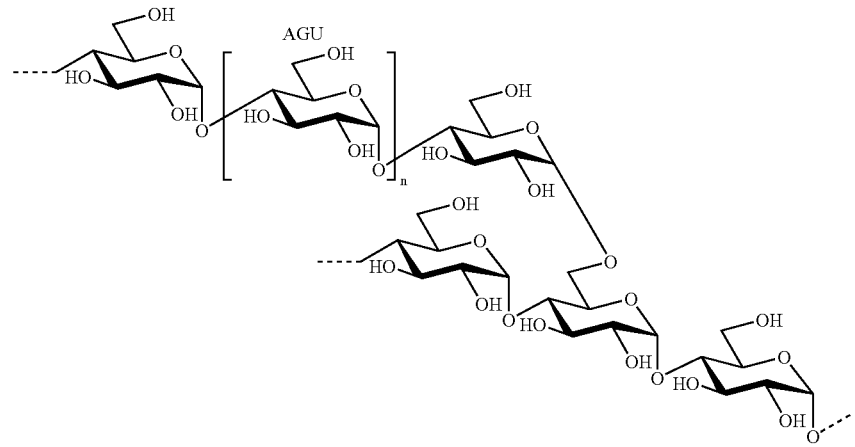

DETAILED DESCRIPTION OF THE INVENTION

The compounds which are used in accordance with the invention exhibit a high degree of biological activity and surprisingly inhibit the growth of pathogenic bacteria, such as staphylococci and mycobacteria, at minimal inhibitory concentrations in the range of 5-60 mg/l, and also inhibit the replication of herpes viruses and influenza viruses in a range of 3-50 mg/l. Because of these properties, the compounds can be used for producing drugs for preventing and controlling bacterial and viral infections. They can be used both on their own and in combination with known therapeutic agents or physiologically tolerated auxiliary and carrier substances.

The antiinfective compounds can be prepared for use as solutions or suspensions in pharmaceutically acceptable media for topical administration, for parenteral administration, by way of intravenous, subcutaneous or intramuscular injections, or for intranasal administration, and as tablets, capsules or suppositories. The compounds can be employed in doses of 0.1-1000 mg/kg of bodyweight.

Polysaccharides, preferably polyglucans such as cellulose, lichenan, pullulan and dextran, and particularly preferably starches, such as native starches of different provenance, for example potato starch, wheat starch, corn starch and rice starch, and starches which have been partially hydrolyzed chemically or enzymically, such as solamyl, FIG. 1 Example of the structure of the polysaccharides which can be employed.

TABLE 1

| Starch material | Amylose content (%) | Molecular weight (GPC[1]) (g · mol$^{-1}$) |
|---|---|---|
| hylon VII (H) | 70 | 9 · 10$^6$ |
| potato starch (P, Emsland) | 28 | 40 · 10$^6$ |
| corn starch (C) | 28 | 76 · 10$^6$ |
| wheat starch (W) | 26 | 65 · 10$^6$ |
| waxy corn starch (WC) | 1 | 51 · 10$^6$ |
| solamyl (S) | 28 | 9700 |

[1]determined in DMSO

The extent to which the hydroxyl groups have been transformed is described by the mean degree of substitution (DS). This mean value indicates, without any differentiation, the number of functionalized hydroxyl groups and is accordingly, in the case of the abovementioned polysaccharides, by definition in the range from 0 to 3. The DS of cationic groups in the polysaccharide derivatives of the invention having an antiinfective effect is between 0.4 and 3.0, preferably between 0.6 and 1.8. If, during derivatizations, functional groups are introduced which themselves contain reactive groups, e.g. hydroxyl groups as a result of the etherification of polysaccharides with epoxides, these latter groups can likewise react, resulting in the formation of longer side chains.

The polysaccharide derivatives which can be used in accordance with the invention are known or can be obtained in a manner known per se, in particular by etherifying polysaccharides with reactive compounds, either thereby directly forming quaternary ammonium compounds of the general formula (I) (PS: polysaccharide residue, only one substituent shown) or with the quaternization taking place after the etherification reaction. In formula (I), $R_1$, $R_2$ and $R_3$ are preferably, independently of each other, alkyl having 1-4 C atoms or benzyl or substituted benzyl (examples of substituents are 1 to 3 alkyl, halogen, alkoxy, carbamoyl, alkoxycarbonyl, cyano and dialkylamino), $R_1$ is also hydrogen, X is an anion (e.g. halide, hydroxide, sulfate, hydrogen sulfate and another anion of inorganic and carboxylic acids), and n can be 2-4.

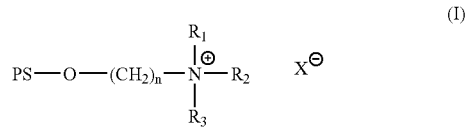
(I)

Quaternary cationizing reagents which are preferably used are 2,3-epoxypropyl-trimethylammonium chloride (QUAB®151, Degussa AG, formula II) or 3-chloro-2-hydroxypropyltrimethylammonium chloride (QUAB® 188, Degussa AG, formula III). Reagents of the general formula IV, in which Y=Cl or Br and n 1-3, can also be used for etherifying the polysaccharides.

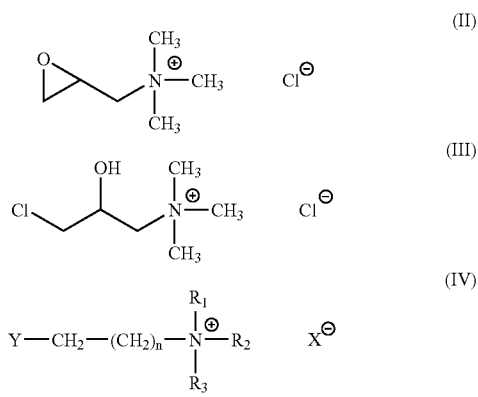

Accordingly, the linker by way of which the quaternary ammonium groups are bonded to the polysaccharides is $C_2$-$C_4$-alkylene which is optionally substituted by hydroxyl.

The etherification for preparing the biologically active polysaccharide derivatives can be carried out in different ways and takes place in a manner which is known per se, with high contents of the cationic groups being achieved. Both suspensions of the polymers in an alcohol and sodium hydroxide solution and water (heterogeneous method), with alcohols such as methanol, isopropanol and, preferably ethanol, or aqueous alkali metal hydroxide solutions, preferably sodium hydroxide solution/water with a transition from the heterogeneous to the homogeneous system, and also homogeneous solutions of the polymers in dipolar aprotic solvents such as dimethyl sulfoxide or dimethylacetamide in the presence of lithium chloride or other solvents as reaction media, are suitable. The time required for the reaction with the cationizing reagent is between 1 and 48 h, preferably from 3 to 24 h, and the temperature is between 30 and 130° C., preferably from 40 to 80° C. In addition, the degree of substitution of the products can be determined, and varied within wide limits, by the molar equivalents of the etherifying agent which are employed. In addition to this, multistep reactions for obtaining the polysaccharide derivatives are also suitable, with a product which is already cationized or amino-functionalized being once again reacted under the abovementioned conditions. Customary methods of polymer chemistry are used to work up the reaction products, with the low molecular weight byproducts and reagent residues being separated off by means of dialysis or washing processes or reprecipitating from water in organic solvents.

The degrees of substitution are calculated using nitrogen values determined by elemental analysis, in accordance with the following defining formula:

$$DS_N = \frac{162.15 \cdot \% \, N}{1401 - 151.64 \cdot \% \, N}$$

In addition to this, the counterions, such as chloride, which are present in the compounds, and the NMR spectra, are suitable for determining the DS values.

The following implementation examples are intended to explain the invention in more detail but without restricting it in any way.

IMPLEMENTATION EXAMPLES

1. Preparing the Compounds by Conducting a Heterogeneous Reaction in Ethanol/Sodium Hydroxide Solution/Water 20 g of polysaccharide (nature of the polysaccharide, see the following table 2) are suspended in 80 ml of ethanol. A solution of 10.85 g of NaOH in 28 ml of water and 80 ml of ethanol, and also a solution of 0.246 mol of QUAB®188 (69% aqueous solution), are added dropwise to this suspension. The reaction mixture is stirred at 60° C. for 6 h. The product is neutralized with 0.1 N HCl, dialyzed and freeze-dried.

The yield is 95% (based on the DS achieved). Elemental analysis: N 3.51% Mean degree of substitution ($DS_N$)=0.66

TABLE 2

Heterogeneous cationization

| Polysaccharide | Type | Reagent Molar ratio AGU:Reagent | Product | Degree of substitution |
|---|---|---|---|---|
| Hylon | QUAB ® 188 | 1:3 | H 1 (466) | 0.50 |
| Hylon | QUAB ® 188 | 1:2 | H 2 (KS005) | 0.66 |
| Amioca | QUAB ® 188 | 1:3 | WC 1 (505) | 0.14 |
| Potato starch | QUAB ® 188 | 1:3 | P 1[1] (491) | 0.34 |
| Potato starch | QUAB ® 188 | 1:3 | P 2[1] (469) | 0.58 |
| Wheat starch | QUAB ® 188 | 1:3.25 | W 1 (527) | 0.99 |
| Wheat starch | QUAB ® 188 | 1:2 | W 3 (571) | 0.61 |
| Wheat starch | [2] | 1:5 | W 4 | 0.72 |
| Wheat starch | [2] | 1:10 | W 5 | 0.81 |

[1]different NaOH concentration
[2]reagent: Cl—$CH_2$—$CH_2$—$N(C_2H_5)H_2Cl$

2. Conversion of Polysaccharides in Aqueous Sodium Hydroxide Solution 20 g of polysaccharide (nature of polysaccharide, see following table 3) are suspended in a sodium hydroxide solution (0.5 g of NaOH in 100 ml of water). The mixture is stirred at 60° C. for one hour. 0.123 mol of QUAB®151 or, in the case of the degraded starch solamyl, QUAB® 188, is added dropwise at this temperature. The reaction mixture is stirred at 60° C. for 6 h. After cooling down to room temperature, the mixture is neutralized with 0.1 N HCl; it is then dialyzed and the product freeze-dried.

The yield is 98% (based on the DS achieved). Elemental analysis: N 3.34% Mean degree of substitution ($DS_N$)=0.60

TABLE 3

Heterogeneous/homogeneous cationization

| Polysaccharide | Reagent Type | Molar ratio AGU:Reagent | Product | Degree of substitution |
|---|---|---|---|---|
| Hylon | QUAB ® 151 | 1:1 | H 3 (477) | 0.40 |
| Hylon | QUAB ® 151 | 1:2 | H 4 (KS006) | 0.92 |
| Amioca | QUAB ® 151 | 1:0.5 | WC 2 (503) | 0.38 |
| Amioca | QUAB ® 151 | 1:1 | WC 3 (501) | 0.60 |
| Amioca | QUAB ® 151 | 1:2 | WC 4 (502) | 0.92 |
| Corn starch | QUAB ® 151 | 1:0.5 | C 1 (517) | 0.35 |
| Corn starch | QUAB ® 151 | 1:1 | C 2[1] (516) | 0.55 |
| Corn starch | QUAB ® 151 | 1:1 | C 3[1] (519) | 0.72 |
| Corn starch | QUAB ® 151 | 1:2 | C 4 (515) | 1.03 |
| Potato | QUAB ® 151 | 1:3 | P 3 (KS 016) | 0.69 |
| Potato | QUAB ® 151 | 1:2 | P 4 (KS 013) | 1.05 |
| Wheat starch | QUAB ® 151 | 1:0.5 | W 4 (520) | 0.39 |
| Solamyl | QUAB ® 188 | 1:2 | S 1[1] (554) | 0.68 |
| Solamyl | QUAB ® 188 | 1:3 | S 2 (555) | 0.76 |
| Solamyl | QUAB ® 188 | 1:2 | S 3[1] (568) | 0.80 |

[1]different NaOH concentration

3. Conducting a Homogeneous Reaction in Dimethyl Sulfoxide (DMSO)

15 g of polysaccharide (nature of the polysaccharide, see following table 4) are suspended in dimethyl sulfoxide (DMSO) at room temperature and the suspension is heated to 80° C., in connection with which the polysaccharide dissolves. The solution is cooled down to room temperature and 0.5 g of NaOH, dissolved in 20 ml of water, is added. 0.0925 mol of QUAB®151 is then added dropwise, while stirring. The reaction mixture is stirred at 60° C. for 24 h. After it has been cooled down to room temperature, the mixture is neutralized with 0.1 N HCl and then dialyzed and freeze-dried.

The yield is 99% (based on the DS achieved). Elemental analysis: N 3.22% Mean degree of substitution ($DS_N$)=0.57

TABLE 4

Homogeneous cationization

| Polysaccharide | Reagent Type | Molar ratio AGU:Reagent | Product | Degree of substitution |
|---|---|---|---|---|
| Hylon | QUAB ® 151 | 1:3 | H 5 (436) | 0.55 |
| Potato starch | QUAB ® 151 | 1:1 | P 5 (KS 9) | 0.42 |
| Amioca | QUAB ® 151 | 1:1 | WC 5 (504) | 0.57 |
| Wheat starch | QUAB ® 151 | 1:1 | W 5 (531) | 0.41 |

TABLE 4-continued

Homogeneous cationization

| Polysaccharide | Reagent Type | Molar ratio AGU:Reagent | Product | Degree of substitution |
|---|---|---|---|---|
| Corn starch | QUAB ® 151 | 1:1 | C 5 (532) | 0.40 |
| Solamyl | QUAB ® 151 | 1:1 | S 4 (588) | 0.60 |

4. Cationization in Several Steps 5 g of cationized polysaccharide (nature of the polysaccharide, see following table 5) are suspended in a sodium hydroxide solution (0.5 g of NaOH in 100 ml of water).

The mixture is stirred at 60° C. for one hour. 0.2 mol of QUAB® 151 is added dropwise at this temperature. The reaction mixture is stirred at 60° C. for 6 h. After it has been cooled down to room temperature, the mixture is neutralized with 0.1 N HCl and then dialyzed and freeze-dried.

The yield is 95% (based on the DS achieved). Elemental analysis: N 5.11% Mean degree of substitution ($DS_N$)=1.32

TABLE 5

Cationization in several steps

| Cationized starch | | Reagent | | | Degree of |
|---|---|---|---|---|---|
| Polysaccharide | Initial DS | Type | AGU:Reag. molar ratio | Product | substit. $DS_N$ |
| Hylon | 0.40 | QUAB ® 151 | 1:2 | H 6 (479) | 0.90 |
| Hylon | 0.80 | QUAB ® 151 | 1:1.5 | H 7 (498) | 1.10 |
| Potato | 0.77 | QUAB ® 151 | 1:2 | P 6 (506) | 1.18 |
| Potato | 0.42 | QUAB ® 151 | 1:10 | P 7 (597) | 1.32 |
| Amioca | 0.60 | QUAB ® 151 | 1:10 | WC 6 (598) | 1.25 |
| Wheat | 0.41 | QUAB ® 151 | 1:10 | W 6 (603) | 1.16 |
| Wheat | 0.88 | QUAB ® 151 | 1:10 | W 7 (602) | 1.41 |
| Corn | 0.55 | QUAB ® 151 | 1:10 | C 6 (600) | 1.13 |
| Potato | 1.32 | QUAB ® 151 | 1:15 | P 8 | 1.80 |
| Corn | 1.13 | QUAB ® 151 | 1:10 | C 7 | 1.65 |
| Solamyl | 0.80 | QUAB ® 151 | 1:2 | S 5 (610) | 0.91 |

5. Determining the Antibacterial/Antimicrobial Activity of the Compounds Against Gram-positive and Gram-negative Bacteria and Against Yeasts.

The antibacterial activity of the compounds, as directed against *Staphylococcus aureus* SG 511, *S. aureus* 134/93 (multiresistant) and *Mycobacterium vaccae* IMET 10670, was tested by means of determining the minimum inhibitory concentrations (MHCs) in a microbroth dilution test in Müller-Hinton broth (DIFCO) in accordance with the NCCLS guidelines [National Committee for Clinical Laboratory Standards: Methods for dilution antimicrobial susceptibility tests for bacteria that grow aerobically; 4th ed.; Villanova, Ed.; Approved standard Document M7-A4. NCCLS, (1997)]. The results are shown in table 6.

TABLE 6

Antibacterial activity

| | | MHC [mg/l] | |
|---|---|---|---|
| | Degree of substitution | *Staphylococcus aureus* | *Mycobacterium vaccae* |
| Sample | $DS_N$ | SG 511 | 134/93 | IMET10670 |
|---|---|---|---|---|
| H 4 KS006 | 0.92 | 15.6 | 15.6 | 7.8 |
| H 7 498 | 1.10 | 15.6 | 15.6 | 7.8 |
| WC 4 502 | 0.92 | 31.25 | 62.5 | 15.6 |
| C 3 519 | 0.72 | 15.6 | 62.5 | 7.8 |
| C 4 515 | 1.03 | 31.25 | 62.5 | 15.6 |
| P 3 016 | 0.69 | 31.25 | 62.5 | 7.8 |
| P 4 013 | 1.05 | 15.6 | 125 | 3.9 |
| W 2 567 | 0.57 | 62.5 | 62.5 | 15.6 |
| W 3 571 | 0.61 | 31.25 | 31.25 | 7.8 |
| W 1527 | 0.99 | 31.25 | 31.25 | 15.6 |
| S 1 554 | 0.68 | 31.25 | 62.6 | 15.6 |
| S 2 555 | 0.76 | 15.6 | 31.25 | 7.8 |
| S 3 568 | 0.80 | 15.6 | 15.6 | 7.8 |

6. Determining the Antiviral Effect in Regard to Herpes Simplex Virus Type 1

Prior to the antiviral investigations, the 50% cytotoxic concentration ($CC_{50}$) in Green monkey kidney (GMK) cells was determined in order to be able to exclude nonspecific substance effects. To do this, continuous GMK cell lawns in microtiter plates are inoculated with the appropriate substance dilution series (factor 2) (Sclmidtke et al.; J. Virol. Meth. 95, 2001, 133). After a 72-hour incubation, the cells are stained with crystal violet/methanol. After the dye has been leached out, the optical densities of the individual wells are measured (550/630 nm) in a Dynatech plate photometer and compared with the mean value for 6 untreated cell controls, which value is taken to be 100%. The $CC_{50}$ is the substance concentration at the point where the extinction curve of the dilution series intersects with the 50% line of the mean value for the control. The antiviral effect of the compounds in regard to HSV-1 was investigated in a cytopathic effect-inhibiting test (CPE-inhibiting test) performed in GMK cells, and the 50% inhibitory dose ($IC_{50}$) was determined (Schmidtke et al.; J. Virol. Meth. 95, 2001, 133). The selection index was calculated as the ratio of $CC_{50}$ to $IC_{50}$ (table 7).

The starting compounds (QUAB reagents and unmodified starches) did not exhibit any antiviral effect (results not shown).

TABLE 7

Antiviral activity

| Sample | Degree of substitution $DS_N$ | $CC_{50}$ (µg/ml) in GMK cells | $IC_{50}$ (µg/ml) against HSV-1 | Selection index ($CC_{50}/IC_{50}$) |
|---|---|---|---|---|
| H 3 477 | 0.40 | >200 | 8.54 | >23.42 |
| H 1 466 | 0.50 | >200 | 5.11 | >39.14 |
| H 2 005 | 0.66 | >200 | 7.07 | >28.29 |
| WC 2 503 | 0.38 | >200 | 7.05 | >28.37 |
| C 1 517 | 0.35 | >200 | 7.84 | >25.51 |
| P 1 491 | 0.34 | >200 | 10.15 | >19.70 |
| W 4 520 | 0.39 | >200 | 10.55 | >18.96 |
| S 1 554 | 0.68 | 141.54 | 3.59 | 39.43 |

7. Determining the Mode of Action in a Modified PRT

The investigations into the mechanism of action of the substance were carried out in a modified PRT using the acyclovir-sensitive and phosphonoformic acid-sensitive HSV1 strain Kupka and taking the compound M 1 as an example (Schmidtke et al.; J. Virol. Meth. 95, 2001, 133). In the test, the substance was added at various concentrations:

1. only to cell-free virus ($10^6$ pfU/ml), which was then incubated with the compound at 37° C. for 6 h and, after the substance had been diluted, incorporated in the PRT: no plaque reduction in the dose range up to 6.25-25 µg/ml (results not shown),
2. only to the agar: no plaque reduction in the dose range 6.25-25 µg/ml (results not shown),
3. only during the one-hour adsorption, at 4° C. for 2 h (3.12-12.5 µg/ml), and
4. 1, 2 and 4 h before adding virus (3.12-12.5 µg/ml).

The results of the investigations into the mechanism of action show that the compounds according to the invention do not have a virucidal effect since it was not possible to observe any inactivation of cell-free virus. Instead, the prerequisite for inhibiting herpes virus replication is for the substance to be present before or during the adsorption of the virus to the test cells.

The invention claimed is:

1. A method of inhibiting the growth of pathogenic bacteria or the replication of herpes or influenza viruses in a patient comprising the step of administering to said patient an amount of an alpha-glycosidically linked starch polysaccharide derivative represented by general formula I,

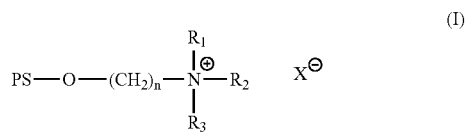

wherein said alpha-glycosidically linked starch polysaccharide derivative has a degree of quaternary ammonium group substitution of from 0.4 to 2.0, n is 2-4, $R_1$ is selected from the group consisting of $C_{1-4}$ alkyl, benzyl and benzyl substituted with a member selected from the group consisting of $C_{1-3}$ alkyl, halogen, alkoxy, carbamoyl, alkoxycarbonyl, cyano, dialkylamino and hydrogen, $R_2$ and $R_3$ are each independently selected from the group consisting of $C_{1-4}$ alkyl, benzyl and benzyl substituted with a member selected from the group consisting of $C_{1-3}$ alkyl, halogen, alkoxy, carbamoyl, alkoxycarbonyl, cyano and dialkylamino, and X is an anion selected from the group consisting of halide, hydroxide, sulfate, hydrogen sulfate and carboxylate, effective to inhibit the growth of said pathogenic bacteria or the replication of said herpes virus or said influenza virus.

2. The method of claim 1 wherein said alpha-glycosidically linked starch polysaccharide derivative is administered at a minimal inhibitory concentration of from 5 to 60 mg/l.

3. The method of claim 1 wherein said alpha-glycosidically linked starch polysaccharide derivative is administered at a minimal inhibitory concentration of from 3 to 50 mg/l.

4. The method of claim 1 wherein said alpha-glycosidically linked starch polysaccharide derivative is administered at a dose of 0.1 to 1000 mg/kg of body weight of said patient.

5. The method of claim 1 wherein said alpha-glycosidically linked starch polysaccharide derivative has a degree of quaternary ammonium group substitution of from 0.6 to 1.8.

6. The method of claim 1 wherein the starch polysaccharide of said alpha-glycosidically linked starch polysaccharide derivative is selected from the group consisting of potato starch, wheat starch, corn starch, rice starch and combinations thereof.

7. The method of claim 1 wherein the starch polysaccharide of said alpha-glycosidically linked starch polysaccharide derivative is selected from the group consisting of starches partially hydrolyzed by chemical means, starches partially hydrolyzed by enzymatic means, starches obtained from genetically modified plants and combinations thereof.

8. The method of claim 1 wherein said alpha-glycosidically linked starch polysaccharide derivative is administered in a form selected from the group consisting of solutions, suspensions, tablets, capsules, suppositories and combinations thereof.

9. The method of claim 8 wherein said alpha-glycosidically linked starch polysaccharide derivative is administered by means selected from the group consisting of parenteral administration, intravenous injection, subcutaneous injection, intramuscular injection, intranasal administration and combinations thereof.

10. The method of claim 1 wherein said pathogenic bacteria are selected from the group consisting of staphylococci and mycobacteria.

11. The method of claim 1 wherein said pathogenic bacteria are staphylococci.

12. The method of claim 11 wherein said pathogenic bacteria are *Staphylococcus aureus*.

13. The method of claim 1 wherein said pathogenic bacteria are mycobacteria.

14. The method of claim 13 wherein said pathogenic bacteria are *Mycobacterium vaccae*.

* * * * *